United States Patent
Kitagawa

(10) Patent No.: US 6,860,137 B2
(45) Date of Patent: Mar. 1, 2005

(54) LIQUID TRANSFER DEVICE, CONTROL METHOD OF LIQUID MIXING RATIO THEREOF AND LIQUID CHROMATOGRAPH WITH LIQUID TRANSFER DEVICE

(75) Inventor: Takaei Kitagawa, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 0 days.

(21) Appl. No.: 10/058,021

(22) Filed: Jan. 29, 2002

(65) Prior Publication Data

US 2002/0112530 A1 Aug. 22, 2002

(30) Foreign Application Priority Data

Feb. 16, 2001 (JP) .......................................... 2001-040771

(51) Int. Cl.[7] .............................. G01N 35/10; F17D 3/00
(52) U.S. Cl. ...................... 73/1.02; 73/61.56; 73/61.55; 73/61.57; 137/3
(58) Field of Search ................................ 73/1.02, 1.06, 73/1.73, 61.55, 61.56, 61.57, 1.36; 137/3

(56) References Cited

U.S. PATENT DOCUMENTS

| | | | | |
|---|---|---|---|---|
| 2,462,995 A | * | 3/1949 | Ritzmann | 422/62 |
| 2,977,199 A | * | 3/1961 | Allington | 137/3 |
| 3,398,689 A | * | 8/1968 | Quittner | 417/338 |
| 3,987,808 A | * | 10/1976 | Carbonell et al. | 137/3 |
| 4,239,623 A | * | 12/1980 | Schrenker | 73/61.52 |
| 4,311,586 A | * | 1/1982 | Baldwin et al. | 73/61.56 |
| 4,595,496 A | * | 6/1986 | Carson | 210/198.2 |
| 5,712,481 A | * | 1/1998 | Welch et al. | 250/339.12 |
| 5,924,794 A | * | 7/1999 | O'Dougherty et al. | 366/136 |
| 6,224,778 B1 | * | 5/2001 | Peltzer | 137/3 |
| 6,374,845 B1 | * | 4/2002 | Melendez et al. | 137/3 |
| 6,463,941 B1 | * | 10/2002 | Takita | 134/57 R |

FOREIGN PATENT DOCUMENTS

JP            3113365 A   *   3/1991  ............... 73/61.56

* cited by examiner

Primary Examiner—Michael Cygan
(74) Attorney, Agent, or Firm—Manabu Kanesaka

(57) ABSTRACT

In obtaining an accurate mixing ratio of a liquid mixture, an actual mixing ratio of at least two different liquids mixed together is obtained, wherein the two kinds of liquids have a predetermined mixing ratio and are mixed by setting switching valves for the liquids. A mixing ratio error is calculated as a difference between the actual mixing ratio and the predetermined mixing ratio, and is stored. A switching timing of the switch valves is corrected based on the stored mixing ratio error.

10 Claims, 4 Drawing Sheets

LIQUID TRANSFER DEVICE, CONTROL METHOD OF LIQUID MIXING RATIO THEREOF AND LIQUID CHROMATOGRAPH WITH LIQUID TRANSFER DEVICE

BACKGROUND OF THE INVENTION AND RELATED ART STATEMENT

The invention relates to a liquid transfer device, a control method for maintaining an accurate mixing ratio of liquid mixture by correcting a switching timing of switching valves thereof and a liquid chromatograph with the liquid transfer device. More specifically, it relates to the liquid transfer device including a plurality of switch valves for switching liquids at a predetermined ratio and having a low-pressure gradient function for transferring a mobile phase through sequential suctions of a mixture of liquids by switching the switch valves; a control method for maintaining an accurate mixing ratio of liquid mixture by correcting a switching timing of the switch valves of the liquid transfer device; and a liquid chromatograph including such a liquid transfer device.

A structure of a conventional liquid chromatograph is shown in FIG. 4.

The liquid chromatograph includes a plunger reciprocation type pump having a low-pressure gradient function as a liquid transfer device. The pump is basically formed of a plunger 1, a pump chamber 3, check valves 5, 7 provided on inlet and outlet sides of the pump chamber 3. Further, the pump includes a motor 9, such as a pulse motor, for driving the pump. A cam 11 is driven by the motor 9 thus causing reciprocation movements of the plunger 1.

Liquids to be mixed are liquid A and liquid B, and passages for transferring the respective liquids to the pump chamber 3 are joined together at a merging point 13 on the side of the check valve 5 connected to the pump chamber 3. Switch valves VA and VB are disposed on the respective passages between the merging point 13 and the liquid A and between the merging point 13 and the liquid B.

The switch valves VA and VB are opened or closed by a control portion 15 in synchronization with the suction cycle. More specifically, the control portion 15 obtains a position of the plunger 1 based on a detection signal of a position sensor 17 for detecting a rotation quantity of the motor 9, and controls the switching timing of the switch valves VA and VB in each suction cycle (i.e. during movement of the plunger 1 from a top dead point to a bottom dead point) based on the position of the plunger 1.

The discharge side of the pump chamber 3 is connected to a mixer 19 for mixing the liquids through the check valve 7. A passage from the mixer 19 is connected to one end of a column 23 for separating a sample through an injector 21 for injecting the sample. The other end of the column 23 is connected to an ultra violet detector (hereinafter referred to as UV detector) 25 for detecting the seperated sample.

Hereunder, the control of the switching timing of the switch valves VA and VB will be explained. When the suction cycle starts, the switch valve VA is opened and the switch valve VB is closed. When the plunger 1 reaches a position X, the switch valve VA is closed and the switch valve VB is opened. The position X is determined according to the mobile phase composition, i.e. a mixing ratio of liquid A and liquid B. The mixing ratio is determined beforehand and stored in the control portion 15.

When the opening or closing of the switch valves VA and VB is controlled as described above, liquid A is sucked into the pump chamber 3 during a period from start of the suction to the position X, and liquid B is sucked into the pump chamber 3 after the plunger 1 reaches the position X. Through movement of the plunger 1 from a bottom dead point to a top dead point, the liquid A and liquid B are mixed in the mixer 19 and transferred with a predetermined mixing ratio.

In the plunger reciprocation type pump of a low-pressure gradient system using switch valves, there has been a problem such that in case there is a displacement among the axes of a disk to which the position sensor 17 is disposed, motor 9 and cam 11, the suction start point, i.e. top dead point, is also displaced, so that it is impossible to obtain an accurate mixing ratio. Also, there has been a problem such that in case there is a machining error of the cam 11, a response delay, or a discrepancy in response speeds at the timing of opening or closing of the respective switch valves, an error is made between the predetermined mixing ratio and the mixing ratio of the liquids actually transferred. Further, there has been a problem such that the mixing ratio error as described above is different in every device.

In view of the above problems, the present invention has been made and an object of the invention is to provide a correcting method for controlling an error between a mixing ratio of an actually transferred mobile phase and a predetermined mixing ratio of the mobile phase.

Another object of the invention is to provide a liquid transfer device having a function as described above.

A further object of the invention is to provide a liquid chromatograph having the function as described above.

Further objects and advantages of the invention will be apparent from the following description of the invention.

SUMMARY OF THE INVENTION

In the present invention, a correcting method for correcting a switching timing of switch valves of a liquid transfer device has a low-pressure gradient function, wherein the switch valves for switching liquids are disposed on an inlet side and a mobile phase is transferred by sequentially sucking a plurality of liquids through the switch valves at a predetermined timing in each it suction cycle. The method comprises determining an actual mixing ratio of the mobile phase with a predetermined mixing ratio of the mobile phase; calculating and storing a mixing ratio error between the actual mixing ratio and the predetermined mixing ratio of the mobile phase; and correcting the switching timing of the switch valves based on the stored mixing ratio error.

In the present invention, a liquid transfer device has a slow-pressure gradient function wherein a plurality of switch valves for switching liquids to be sucked is disposed on an inlet side and a mobile phase is transferred by sequentially sucking a plurality of liquids through the switch valves at a predetermined timing in each suction cycle. The liquid transfer device includes: a mixing ratio calculation portion for determining an actual mixing ratio of the mobile phase with a predetermined mixing ratio based on a detection signal from an outer portion; a mixing ratio error calculating portion for calculating a mixing ratio error between the actual mixing ratio determined by the mixing ratio calculation portion and the predetermined mixing ratio of the mobile phase; a memory portion for storing the mixing ratio error calculated by the mixing ratio error calculation portion; and a valve-switching-timing correction portion for correcting the switching timing of the switch valves based on the mixing ratio error stored in the memory portion.

In the present invention, a liquid chromatograph includes a liquid transfer device having a low-pressure gradient function wherein a plurality of switch valves for switching liquids to be sucked is provided on an inlet side and a mobile phase is transferred by sequentially sucking a plurality of liquids through switch valves at a predetermined timing in each suction cycle. The liquid chromatograph comprises: a mixing ratio calculation portion for determining an actual mixing ratio of the mobile phase with a predetermined mixing ratio based on a detection signal from an outer portion; a mixing ratio error calculation portion for calculating a mixing ratio error as a difference between the actual mixing ratio calculated by the mixing ratio calculation portion and the predetermined mixing ratio of the mobile phase; a memory portion for storing the mixing ratio error calculated by the mixing ratio error calculation portion; and a valve-switching-timing correction portion for correcting the switching timing of the switch valves based on the mixing ratio error stored in the memory portion.

In the specification, a mixing ratio which is fixed in advance is called as a predetermined mixing ratio; a mixing ratio of the mobile phase transferred by switching the switch valves based on the predetermined mixing ratio of the mobile phase is called as a calculation mixing ratio; and an error as a difference between the calculation mixing ratio and the predetermined mixing ratio is called as a mixing ratio error.

With respect to the mobile phase with a predetermined mixing ratio based on a detection signal from an outer portion, a calculation mixing ratio of liquids constituting the mobile phase is obtained. In the liquid transfer device and liquid chromatograph of the present invention, the calculation mixing ratio of the mobile phase is calculated at a mixing ratio calculation portion.

The mixing ratio error as a difference between the calculation mixing ratio and the predetermined mixing ratio of the mobile phase is calculated. In the liquid transfer device and the liquid chromatograph of the present invention, the mixing ratio error is calculated in the mixing ratio error calculation portion.

The switching timing of the switch valves is corrected based on the mixing ratio error. In the liquid transfer device and the liquid chromatograph of the present invention, the switching timing of the switch valves is corrected at the valve switching timing correcting portion.

The switching timing of the switch valves is corrected such that in case the calculation mixing ratio of a liquid to be measured (hereinafter referred to as object liquid) among a plurality of liquids for constituting the mobile phase is smaller than the predetermined mixing ratio with respect to the mixing ratio error, a mixing quantity of the object liquid is increased based on the degree of the mixing ratio error.

In case the calculation mixing ratio of the object liquid is larger than the predetermined mixing ratio with respect to the mixing ratio error, the switching timing of the switch valves is controlled such that the mixing quantity of the object liquid is reduced based on the degree of the mixing ratio error.

In the liquid transfer device and the liquid chromatograph according to the present invention, the switching timing of the switch valves is corrected every gradient cycle by storing the mixing ratio error calculated at the mixing ratio error calculation portion in the memory portion.

DETAILED DESCRIPTION OF THE PREFERRED EMBODIMENTS

In a liquid chromatograph according to the present invention, a mixing ratio calculation portion can determine a mixing ratio based on a detection signal from a detector for detecting a sample of analysis. As a result, it is not required to provide a separate detector for determining the mixing ratio to thereby simplify an apparatus design.

Figure 1:
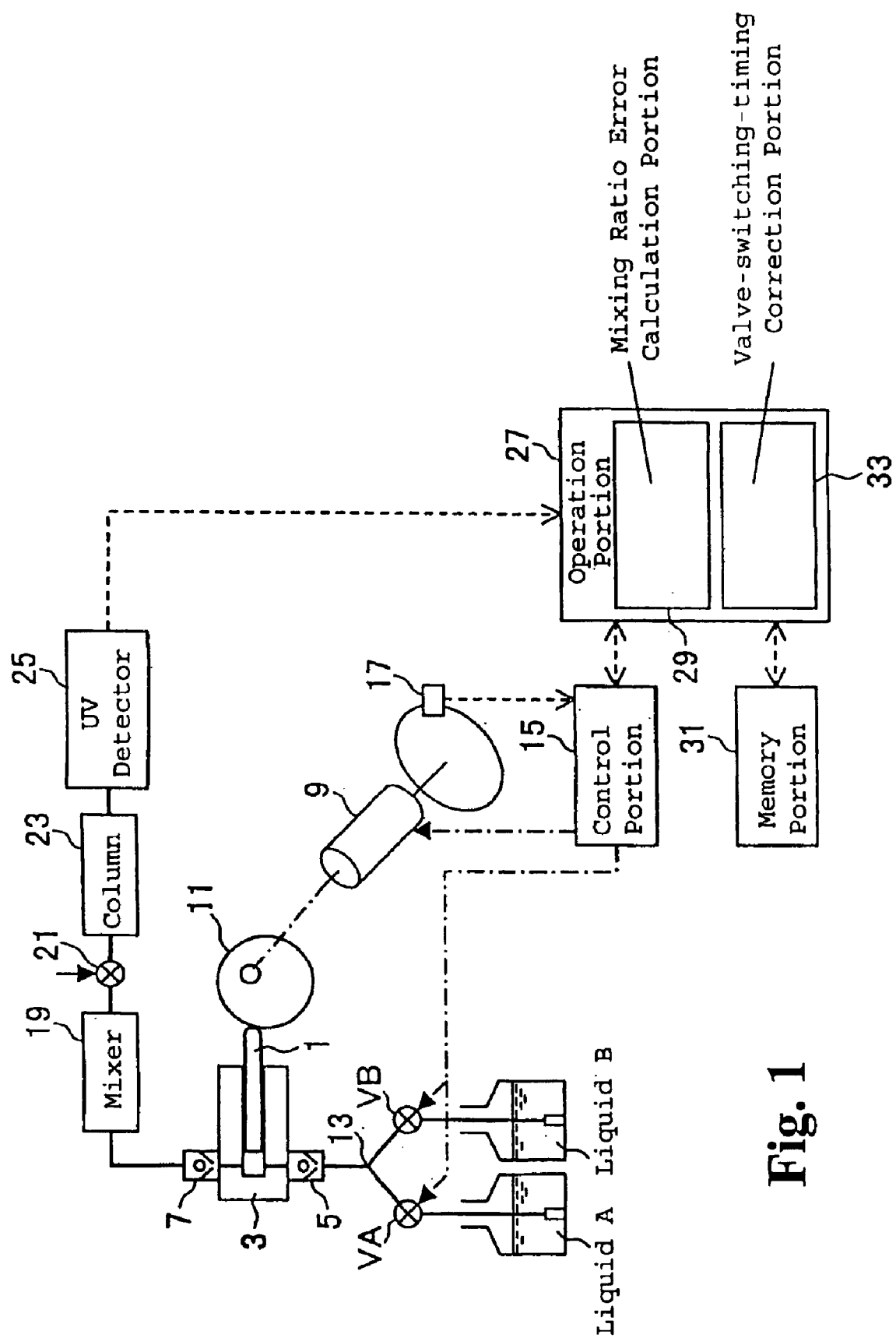
FIG. 1 is a block diagram showing a structure of an embodiment of a liquid chromatograph according to the present invention.

FIG. 1 is a block diagram showing an embodiment of a liquid chromatograph according to the invention.

The liquid chromatograph includes a plunger 1, a pump chamber 3 and check valves 5, 7 for constituting a liquid transfer device. A motor 9 for driving the liquid transfer and a cam 11 are provided thereto. There are used two types of liquids, i.e. liquid A which is pure-water and liquid B (subject liquid) wherein a small amount of acetone is added to pure-water. There are also disposed switch valves VA and VB for switching the liquid A and the liquid B. Reference numeral 13 represents a mixing point of liquids from the switch valves VA and VB. A control portion 15 for switching opening or closing of the switch valves VA and VB is provided. The control portion 15 also controls rotation of the motor 9. A position sensor 17 is provided to a disk rotated in cooperation with rotation of the motor 9. The check valve 7, a mixer 19, an injector 21, a column 23 and a UV detector 23 are connected in series in this order at the outlet side of the pump chamber 3.

The UV detector 25 is electrically connected to an operation portion 27 for processing a detection signal from the UV detector 25. The operation portion 27 detects a separated component based on a detection signal from the UV detector 25; in addition thereto, calculates an acetone concentration of the mobile phase; and determines a mixing ratio of the liquid A and the liquid B based on the acetone concentration. The operation portion 27 stores therein a predetermined mixing ratio of the liquid A and the liquid B.

The mixing ratio calculation portion for constituting the liquid chromatograph of the invention can be materialized by the operation portion 27.

The operation portion 27 includes a mixing ratio error calculation portion 29 for calculating a mixing ratio error between a calculation mixing ratio of the liquids A and B calculated by the operation portion 27 and a predetermined mixing ratio of the liquid A and the liquid B. The operation portion 27 is electrically connected to a memory portion 31 for storing therein the mixing ratio error calculated by the mixing ratio error calculation portion 29. Furthermore, the operation portion 27 includes a valve-switching-timing correction portion 33 for controlling the controlling portion 15 to correct the switching timing of the switch valves VA and VB based on the mixing ratio error stored in the memory portion 31. The controlling portion 15 and the operation portion 27 are electrically connected.

In the embodiment, it is assumed that $B_0$ represents an absorbance shown by the UV detector 25 when only the liquid A (pure water) is transferred as a mobile phase, and $B_{100}$ represents an absorbance shown by the UV detector 25 when only the liquid B (acetone water) is transferred as a mobile phase. The absorbance is in proportion to an acetone concentration.

Assuming that in case the mobile phase with a predetermined mixing ratio of the liquid A:100−X % and the liquid B:X % is transferred and the absorbance obtained by the UV detector 25 is $B_x$, the calculation of an actual mixing ratio of the mobile phase, calculated by the operation portion 27, is as follows:

liquid A:

$$100-\{100 \times B_x/(B_{100}-B_0)\} \, [\%]$$

liquid B:

$$100 \times B_x/(B_{100}-B_0) \, [\%].$$

The mixing ratio error calculation portion 29 calculates the mixing ratio error as a difference between the predetermined mixing ratio stored in the controlling portion 15 and the calculation mixing ratio calculated at the operation portion 27, and the result is stored in the memory portion 31 in a nonvolatile manner. Then, the valve-switching-timing correction portion 33 calculates and corrects the opening-closing timing of the switch valves VA and VB from the mixing ratio error, controls the control portion 15 based on the results, and corrects the switching timing of the switch valves VA and VB.

Regarding a correction calculation method at the valve-switching-timing correction portion 33, two calculation examples are shown hereunder as embodiments of the correction method according to the present invention. The correction mentioned hereunder is automatically carried out such that the control portion 15 controls the motor 9; the position sensor 17 controls position of the plunger 1 and switching of the switch valves VA and VB; the operation portion 27 calculates the switching timing of the switch valves VA and VB at the predetermined mixing ratio; and the valve-switching-timing correction portion 33 calculates the mixing ratio error as a difference between the calculation mixing ratio and the predetermined mixing ratio.

Figure 2:
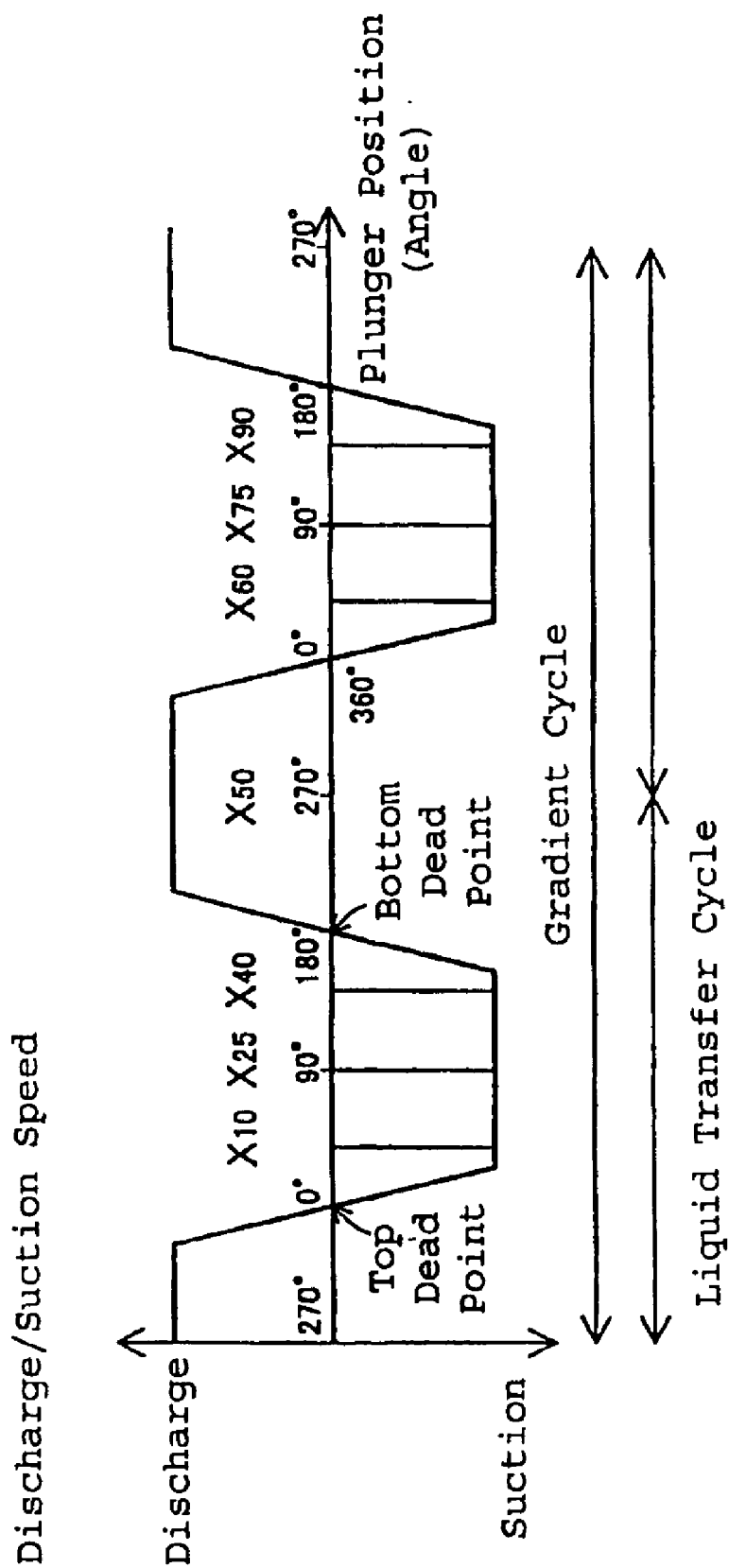
FIG. 2 is a graph showing a relationship between a plunger position (angle) and discharge-suction speeds (discharge quantity and suction quantity per unit time) in the embodiment.

A relationship between a plunger position (angle) and discharge-suction speed (discharge volume and suction volume per unit time) is schematically illustrated in FIG. 2. The graph represents changes in the discharge and suction speeds of the liquid transfer device with time. Since one reciprocation motion of the plunger 1 of the liquid transfer device shown in FIG. 1 corresponds to one cycle of the liquid transfer, two suction cycles are shown as one gradient cycle that corresponds to two reciprocation motions of the plunger 1. The angles are rotation angles of the cam 11.

With reference to FIGS. 1 and 2, examples of the correction calculation in the valve-switching-timing correction portion 33 will be explained.

CALCULATION EXAMPLE 1

In FIG. 2, the rotation angle 0° of the cam 11 corresponds to a top dead point of the plunger 1, and 180° thereof corresponds to a bottom dead point thereof. $X_{25}$ (a mixing ratio of the liquid A is 25%) is achieved at a rotation angle 90° of the cam 11. Assuming that during a rotation angle from 0° to 90° in the first cycle, the switch valve VA is opened and the switch valve VB is closed; and during the rotation angle from 90° to 180° in the first cycle and a rotation angle from 0° to 180° in the second cycle, the switch valve VA is closed and the switch valve VB is opened; theoretically the mobile phase is transferred with a mixing ratio of 25% of the liquid A and 75% of the liquid B.

However, in the actual case, there is a possibility to cause a mixing ratio error due to displacement in a position of the top dead point, machining accuracy of the cam 11, influence of a solvent compression ratio and the likes. In FIG. 2, since the entire suction cycle 180° corresponds to 50% of the mixing ratio, 1% of the mixing ratio corresponds to 3.6° of the rotation angle of the cam 11. Therefore, when a mixing ratio error is −1% (i.e., an actual mixing ratio of the liquid A is 1% below a predetermined value), the valve-switching-timing correction portion 33 carries out a correction calculation such that the top dead point is displaced by −3.6°. Similarly, when a mixing ratio error is +1% (i.e., the mixing ratio of the liquid A exceeds a predetermined value by 1%), the valve-switching-timing correction portion 33 carries out a correction calculation such that the top dead point is displaced by +3.6°. Thus, by controlling an actual switching timing of the switch valves VA and VB, the mobile phase can be transferred with an accurate mixing ratio.

CALCULATION EXAMPLE 2

In FIG. 2, $X_{10}$, $X_{40}$ and $X_{50}$ are theoretical switching angles of the switch valves at A/B (a ratio of the liquid A/the liquid B)=10%/90%, A/B=40%/60% and A/B=50%/50%, respectively. With reference to $X_{50}$, since the plunger 1 is positioned at a middle point of the discharge cycle, A/B=50%/50% can be achieved with a substantial accuracy.

Assuming that an absorbance determined by the UV detector 25 is $B_{50}$ at A/B=50%/50%, and $B_x$ is an absorbance when the liquid A and liquid B are transferred at a predetermined mixing ratio of 100−X % and X %, respectively, an actual mixing ratio of the mobile phase determined by the operation portion 27 is as follows:

Liquid A:

$$100-\{50 \times B_x/(B_{50}-B_0)\} \, [\%]$$

Liquid B:

$$50 \times B_x/(B_{50}-B_0) \, [\%]$$

When the switch valves VA and VB are switched at $X_{10}$ and $X_{40}$, assume that mixing ratio errors as a difference between the calculation mixing ratio and the predetermined mixing ratio are $Y_{10}\%$ and $Y_{40}\%$, respectively.

While the correction is made at one point with respect to one suction cycle in Calculation Example 1, there are two correction points, i.e. $X_{10}$ and $X_{40}$, with respect to one suction cycle in Calculation Example 2. Thus, it is possible to accelerate or delay a switching timing of the switch valve VB when the mixing ratio of the liquid B is close to 10% and 40% based on the mixing ratio errors $Y_{10}\%$, $Y_{40}\%$. As a result, the mixing ratio accuracy in the suction cycle can be further improved.

When the mixing ratio errors are $Y_{10}\%=Y_{60}\%$, $Y_{40}\%=Y_{90}\%$, switching timings at $X_{60}$ and $X_{90}$ can also be subjected in the same fashion. Through the correction in one suction cycle, an entire gradient cycle can be corrected, so that the mobile phase can be accurately transferred within a whole mixing ratio.

When a position of the top dead point is corrected as described in Calculation Example 1 first, and corrections in one cycle are performed by the method in Calculation Example 2 thereafter, one can achieve the mobile phase with a further improved accurate mixing ratio.

Figure 3:
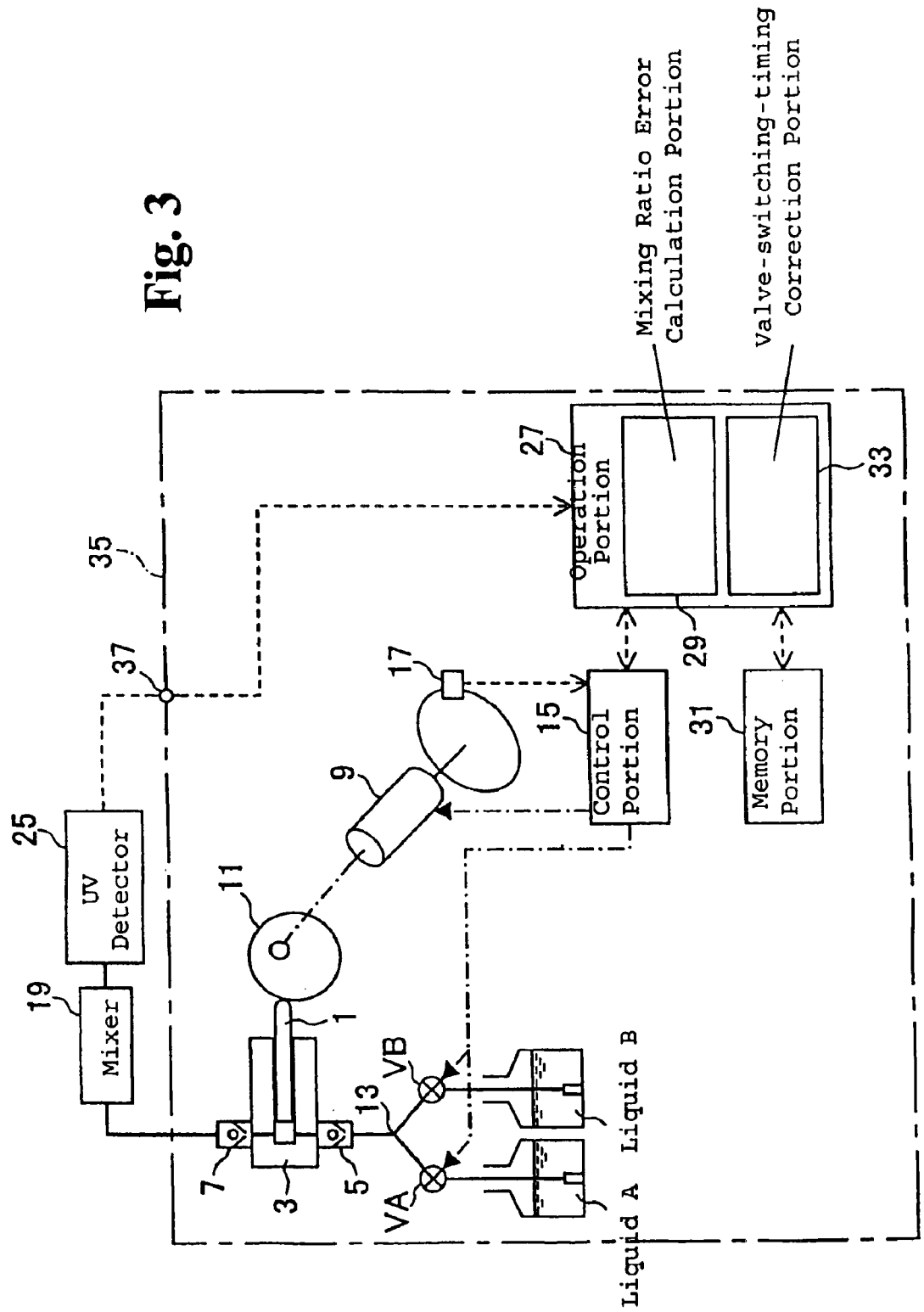
FIG. 3 is a block diagram showing a structure of an embodiment of a liquid transfer device.
Figure 4:
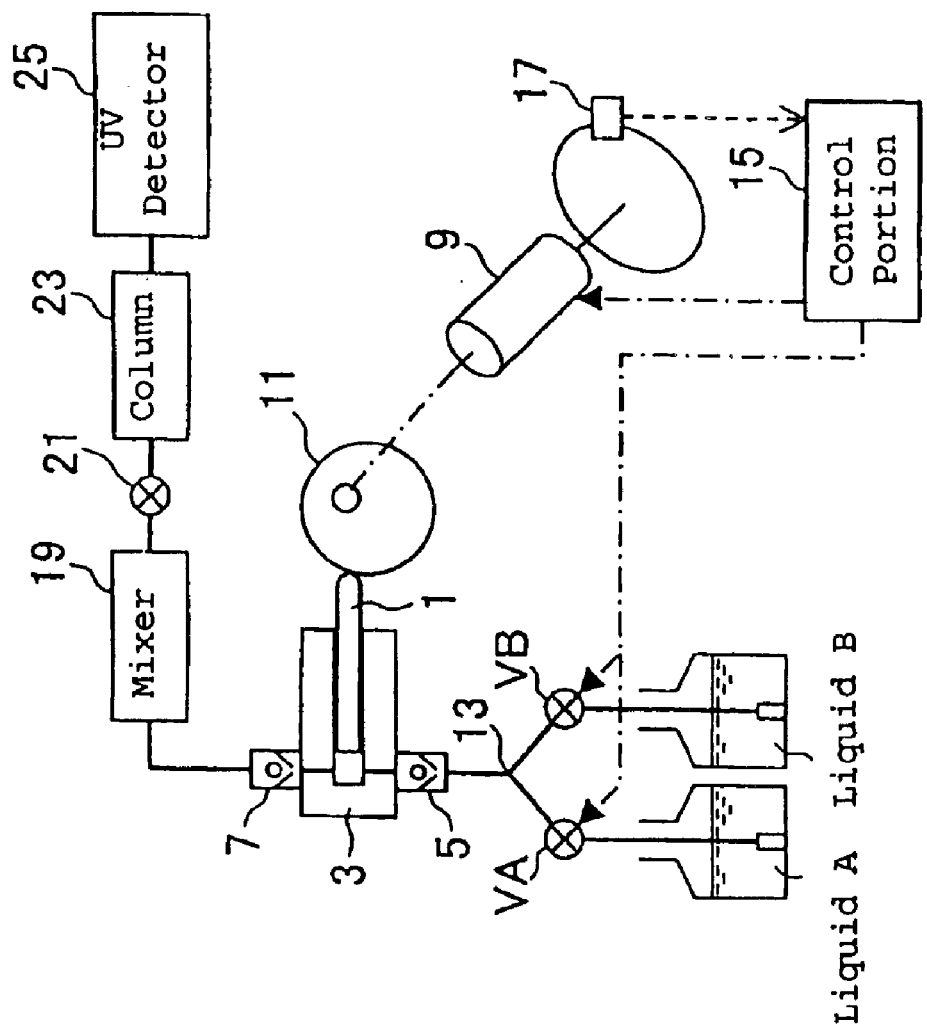
FIG. 4 is a block diagram showing a structure of a conventional liquid chromatograph.

FIG. 3 is a block diagram showing an embodiment of a liquid transfer device according to the present invention. The common portions as those shown in FIG. 1 are represented by the same symbols and their explanations are omitted.

A liquid transfer device 35 includes, as in FIG. 1, a plunger 1, pump chamber 3, check valves 5 and 7, motor 9, cam 11, switch valves VA and VB, control portion 15, position sensor 17, operation portion 27, mixing ratio error calculation portion 29, memory portion 31, and valve switching timing correction portion 33. Liquid A is pure water and liquid B is an acetone water wherein a small amount of acetone is added to pure water. On the discharge side of the pump chamber 3, there are provided a mixer 19 and a UV detector 25 in this order, through the check valve 7. The liquid transfer device 35 includes a terminal 37 for taking a detected signal of the UV detector 25 into the operation portion 27.

A mixing ratio calculation portion for constituting the liquid transfer device of the present invention can be made by the operation portion 27.

When the correction is carried out, the liquid transfer device 35 is operated in the same manner as in FIG. 1 by taking the detected signal of the UV detector 25 into the operation portion 27 through the terminal 37. At that time, it is preferable to provide a passage on the discharge side of the pump chamber 3 with the same resistance as that used as the liquid transfer device in the liquid chromatograph.

In the embodiments of the liquid chromatograph as shown in FIG. 1 and FIG. 3, the switch valves VA and VB for switching two kinds of liquids, i.e. liquid A and liquid B, are provided. However, the present invention is not limited thereto, and in the liquid chromatograph and the liquid transfer device including more than three switch valves corresponding to types of liquids constituting the mobile phase, the correction can be carried out on each switch valve.

Although one gradient cycle consists of two cycles of the liquid transfer device in the aforementioned embodiments, the present invention is not limited thereto. The present invention can be applied to a liquid chromatograph wherein one gradient cycle consists of one cycle or more than three cycles of the liquid transfer device.

Also, although the UV detector is used as a detector for determining a concentration of an object component in the mobile phase in the aforementioned embodiments, the present invention is not limited thereto. Detectors of other types, such as an optical detector using infrared light and visible light and a detector based on refraction index and electric conductivity, may be used.

Additionally, although the calculation mixing ratio is calculated based on the detection signal corresponding to the concentration of an object component in the aforementioned embodiments, the present invention is not limited thereto. The calculation mixing ratio may be calculated based on the detection signal corresponding to the mixing ratio of liquids constituting the mobile phase.

Also, although the present invention is applied to the liquid chromatograph with a single plunger pump of one pump chamber in the aforementioned embodiments, the present invention is not limited thereto. The present invention can be applied to any liquid chromatograph having a liquid transfer device wherein the mobile phase is transferred through the reciprocation movement of the plunger by, for example, series double plunger pump where two pump chambers are connected in series, or parallel double plunger pump where the two pump chambers having check valves on the inlet side and outlet side thereof, respectively, are disposed in parallel.

In the correcting method of the valve switching timing of the liquid transfer device according to the present invention, first, an actual mixing ratio of the mobile phase predetermined by switching the switch valves is obtained. Second, a mixing ratio error as a difference between the obtained actual mixing ratio and the predetermined mixing ratio is calculated and stored. Third, the switching timing of the switch valves is adjusted based on the stored mixing ratio error.

The liquid transfer device according to the present invention includes a mixing ratio calculation portion for calculating an actual mixing ratio of the mobile phase based on a detection signal from an outer device, a mixing ratio error calculation portion for calculating a mixing ratio error as a difference between the mixing ratio predetermined by the switch valves and the actual mixing ratio of the mobile phase calculated by the mixing ratio calculation portion, a memory portion for storing therein the mixing ratio error calculated by the mixing ratio error calculation portion, and a timing correcting portion for correcting a switching timing of the switch valves based on the mixing ratio error stored in the memory portion.

The liquid chromatograph according to the present invention includes a mixing ratio calculation portion for calculating an actual mixing ratio of the mobile phase predetermined by the switch valves, a mixing ratio error calculation portion for calculating a mixing ratio error as a difference between the predetermined mixing ratio and the actual mixing ratio of the mobile phase calculated by the mixing ratio calculation portion, a memory portion for storing therein the mixing ratio error calculated by the mixing ratio error calculation portion, and a timing correcting portion for correcting a switching timing of the switch valves based on the mixing ratio error stored in the memory portion.

In the liquid transfer device, the correcting method of the valve switching timing in the liquid transfer device, and the liquid chromatograph according to the present invention, it is possible to control the valve switching timing based on the mixing ratio error, and the error between an actual mixing ratio of the mobile phase and a predetermined mixing ratio of the mobile phase can be controlled.

While the invention has been explained with reference to the specific embodiments of the invention, the explanation is illustrative and the invention is limited only by the appended claims.

What is claimed is:

1. A method for obtaining an accurate mixing ratio of a liquid mixture in a liquid transfer device with a low pressure gradient function, comprising:

providing a pump chamber having a plunger to provide suction and discharge operations;

mixing at least two different liquids at a predetermined mixing ratio by changing a switching timing of switch valves, said at least two different liquids being held into the pump chamber by operation of the plunger and by switching the switch valves to thereby determine an actual mixing ratio of the at least two different liquids mixed together;

calculating a mixing ratio error as a difference between said actual mixing ratio and said predetermined mixing ratio;

storing said mixing ratio error in a memory;

correcting the switching timing of the switch valves for the at least two different liquids based on said stored mixing ratio error in operating the plunger for a practical operation subsequently performed to thereby obtain the accurate mixing ratio of the at least two different liquids; and sequentially transferring said at least two different liquids as the practical operation by opening and closing the switch valves for the liquids, said switching timing of the switch valves being corrected for subsequent transfer of the at least two different liquids.

2. A liquid transfer device with a low pressure gradient function for transferring a mixture of at least two different liquids as a mobile phase for an analytical apparatus, comprising:

a plurality of switch valves connected to said at least two different liquids, respectively;

a pump having a pump chamber with an outlet and an inlet connected to said switch valves, and a plunger slidably situated in the pump chamber for transferring the liquids to be held in the pump chamber alternately through the switch valves to prepare a mixture thereof;

a mixing ratio calculation portion for determining an actual mixing ratio of the mixture mixed at a predetermined mixing ratio by said pump;

a mixing ratio error calculation portion for calculating a mixing ratio error as a difference between said actual mixing ratio calculated by said mixing ratio calculation portion and the predetermined mixing ratio electrically connected to said mixing ratio calculation portion;

a memory portion for storing said mixing ratio error calculated by said mixing ratio error calculation portion electrically connected to said mixing ratio error calculation portion; and a valve-switching-timing correction portion for correcting a switching timing of the switch valves based on the mixing ratio error stored in said memory portion in operating the plunger for a practical operation subsequently performed to thereby obtain an accurate mixing ratio of the liquids in the practical operation, said valve-switching-timing correction portion being electrically connected to said mixing ratio error calculation portion, said memory portion, and said plurality of switch.

3. A liquid transfer device according to claim 2, wherein said pump further includes a cam connected to the plunger, a motor connected to the cam for reciprocating the plunger, and a position sensor connected to the motor for detecting a position of the plunger through the motor.

4. A liquid transfer device according to claim 3, further comprising a mixer for mixing the mobile phase connected to the outlet of the pump, an injector portion connected to the mixer for injecting a sample into the mobile phase, a column portion for separating the sample connected to the injector portion, and a detector for detecting the sample connected to the column portion.

5. A liquid chromatograph comprises:

a liquid transfer device with a low pressure gradient function including a pump chamber having an inlet and an outlet, a plunger slidably situated in the pump chamber, and a plurality of switch valves connected to the inlet for changing liquids to be transferred at a predetermined timing for transferring the liquids sequentially as a mobile phase by an operation of the plunger to have a predetermined mixing ratio;

a mixing ratio calculation portion for determining an actual mixing ratio of said mobile phase by the liquid transfer device actually operated based on the predetermined mixing ratio;

a mixing ratio error calculation portion for calculating a mixing ratio error as a difference between said actual mixing ratio calculated by said mixing ratio calculation portion and the predetermined mixing ratio electrically connected to said mixing ratio calculation portion;

a memory portion for storing said mixing ratio error calculated by said mixing ratio error calculation portion electrically connected to said mixing ratio error calculation portion; and a valve-switching-timing correction portion for correcting a switching timing of the switch valves based on the mixing ratio error stored in said memory portion in operating the plunger for a practical operation subsequently performed to thereby obtain an accurate mixing ratio of the liquids in the practical operation, said valve-switching-timing correction portion being electrically connected to said mixing ratio error calculation portion, said memory portion, and said plurality of switch valves.

6. A liquid chromatograph according to claim 5, further comprising a detector for obtaining information of the actual mixing ratio of the mobile phase, said mixing ratio calculation portion calculating the actual mixing ratio based on a signal from said detector.

7. A liquid chromatograph according to claim 6, further comprising a mixer for mixing the mobile phase connected to the liquid transfer device, an injector portion connected to the mixer for injecting a sample into the mobile phase, and a column portion for separating the sample connected to the injector portion, said detector being connected to the column portion.

8. A method according to claim 1, wherein in a step of subsequently transferring the at least two different liquids as the practical operation, the switching timing of the switch valves is corrected in every gradient cycle by using the mixing ratio error calculated and stored in the memory.

9. A liquid transfer device according to claim 2, wherein in the valve-switching-timing correction potion, the switching timing of the switch valves is corrected in every gradient cycle by using the mixing ratio error calculated at the mixing ratio error calculation portion and stored in the memory portion.

10. A liquid chromatograph according to claim 5, wherein in the valve-switching-timing correction potion, the switching timing of the switch valves is corrected in every gradient cycle by using the mixing ratio error calculated at the mixing ratio error calculation portion and stored in the memory portion.

* * * * *